(12) United States Patent
Greene et al.

(10) Patent No.: US 8,540,448 B2
(45) Date of Patent: Sep. 24, 2013

(54) COVER STRUCTURE FOR ENCLOSING A REMOVEABLE FLUID-DISPENSING RESERVOIR BETWEEN THE COVER AND AN EXTERIOR SURFACE OF A TOOTHBRUSH

(75) Inventors: Daniel Greene, Seattle, WA (US); Friedrich Stoeffler, Klagenfurt (AT)

(73) Assignee: Koninklijke Philips N.V., Eindhoven (NL)

( * ) Notice: Subject to any disclaimer, the term of this patent is extended or adjusted under 35 U.S.C. 154(b) by 825 days.

(21) Appl. No.: 11/629,765

(22) PCT Filed: Jun. 15, 2005

(86) PCT No.: PCT/IB2005/051975
§ 371 (c)(1),
(2), (4) Date: Jul. 7, 2008

(87) PCT Pub. No.: WO2005/122949
PCT Pub. Date: Dec. 29, 2005

(65) Prior Publication Data
US 2010/0003068 A1   Jan. 7, 2010

Related U.S. Application Data

(60) Provisional application No. 60/580,658, filed on Jun. 17, 2004.

(51) Int. Cl.
*B43K 5/02* (2006.01)
(52) U.S. Cl.
USPC ............... 401/188 R; 401/282; 401/270

(58) Field of Classification Search
USPC ............ 401/270, 274, 278, 268, 183, 184, 401/282, 145, 284, 187, 1, 84, 156; 15/167.1, 15/167.2, 24, 29, 22.1, 22.2; 433/82, 87
See application file for complete search history.

(56) References Cited

U.S. PATENT DOCUMENTS

| | | | | |
|---|---|---|---|---|
| 1,677,194 | A * | 7/1928 | Mendoza | 401/281 |
| 2,536,968 | A * | 1/1951 | Tirocchi et al. | 401/155 |
| 2,841,806 | A * | 7/1958 | Blasi | 15/24 |
| 3,381,325 | A * | 5/1968 | Reineman | 15/104.002 |
| 4,315,741 | A * | 2/1982 | Reichl | 433/82 |
| 4,821,752 | A * | 4/1989 | Widlak | 132/309 |
| 4,991,989 | A * | 2/1991 | Fitjer | 401/155 |
| 5,208,933 | A | 5/1993 | Lustig et al. | |
| 5,700,146 | A | 12/1997 | Kucar et al. | |
| 5,974,618 | A * | 11/1999 | Dumler | 15/167.1 |
| 5,993,180 | A | 11/1999 | Westerhof et al. | |
| 6,164,967 | A | 12/2000 | Sale et al. | |
| 6,179,503 | B1 * | 1/2001 | Taghavi-Khanghah | 401/184 |

(Continued)

FOREIGN PATENT DOCUMENTS
WO   WO 03068466 A1 * 8/2003

*Primary Examiner* — David Walczak
*Assistant Examiner* — Jennifer C Chiang

(57) ABSTRACT

A fluid-dispensing power toothbrush which includes a handle portion with a housing, a head portion and a fluid delivery system. The fluid delivery system includes a fluid reservoir and a fluid pump which are positioned to extend substantially along an outer surface of the housing of the handle portion. A cover member is pivotally attached to the housing and is configured to overlay and mate with a portion of the housing to form the exterior surface of a lower portion of the toothbrush when the cover member is in a closed position.

12 Claims, 5 Drawing Sheets

(56) References Cited

U.S. PATENT DOCUMENTS

| | | |
|---|---|---|
| 6,434,773 B1 * | 8/2002 | Kuo .............................. 15/22.1 |
| 6,536,447 B1 * | 3/2003 | Fioravanti et al. ............. 132/299 |
| 6,622,333 B1 * | 9/2003 | Rehkemper et al. .............. 15/29 |
| 6,623,698 B2 * | 9/2003 | Kuo ............................ 422/68.1 |
| 6,719,471 B1 * | 4/2004 | Giro ........................... 401/188 R |
| 6,766,807 B2 * | 7/2004 | Piccolo et al. ................ 132/309 |
| 6,913,606 B2 * | 7/2005 | Saitou et al. .................. 606/133 |
| 7,213,291 B2 * | 5/2007 | Cheng .......................... 15/104.2 |
| 7,401,373 B2 * | 7/2008 | Tybinkowski et al. ............ 15/29 |
| 8,387,628 B2 * | 3/2013 | Bowie .......................... 132/311 |
| 2004/0057773 A1 * | 3/2004 | Gray ............................ 401/277 |
| 2004/0069317 A1 | 4/2004 | Kemp et al. |
| 2004/0237995 A1 * | 12/2004 | Mualem et al. ............... 132/311 |
| 2008/0137998 A1 | 6/2008 | Burfiend et al. |
| 2009/0136285 A1 | 5/2009 | Hall et al. |
| 2010/0014909 A1 * | 1/2010 | Sampaio ....................... 401/268 |

* cited by examiner

COVER STRUCTURE FOR ENCLOSING A REMOVEABLE FLUID-DISPENSING RESERVOIR BETWEEN THE COVER AND AN EXTERIOR SURFACE OF A TOOTHBRUSH

CROSS REFERENCE TO RELATED APPLICATION

This application claims the benefit of U.S. provisional application Ser. No. 60/580,658 filed 17 Jun. 2004, which is incorporated herein by reference.

This invention relates generally to fluid-dispensing toothbrushes, and more specifically concerns a movable cover member portion of such a toothbrush, the cover member overlaying a fluid reservoir positioned adjacent an exterior surface of a handle portion of the toothbrush.

In most fluid-dispensing power toothbrushes, the reservoir portion, also referred to herein as a cartridge, which contains the fluid, typically has a capacity for a plurality of uses and when empty, is removed and disposed of, replaced by a full reservoir. Such reservoirs must be conveniently accessible to the user, such as by opening a cover in the toothbrush. Difficulties with covers, however, are well known. They are often cumbersome and inconvenient to use. They frequently break, are difficult to replace and are usually not restrained in any way so that they are free to move (flop) around after they have been initially opened.

In general, since space for a reservoir in most fluid-dispensing toothbrushes is at a premium, any cover structure must be arranged to require as little additional space as possible, yet provide the desired result of covering the reservoir.

Accordingly, the present invention is a cover member for a fluid-dispensing power toothbrush, the power toothbrush including a handle portion, a head portion and a fluid system which in turn includes a fluid reservoir which extends substantially entirely along an outer surface of the handle in the assembled toothbrush, the cover member being configured to overlay and mate with a portion of the handle, forming a portion of the exterior surface of a lower portion of the toothbrush when the cover member is in a closed position, wherein the cover member is configured relative to the outer surface of the handle to define a space therebetween to accommodate the fluid reservoir when the cover member is in a closed position, and wherein the fluid reservoir is accessible for removal when the cover member is in its open position; and a connector assembly for movably attaching the cover member to the handle to permit the cover member to move between said open and closed positions.

Figure 1:
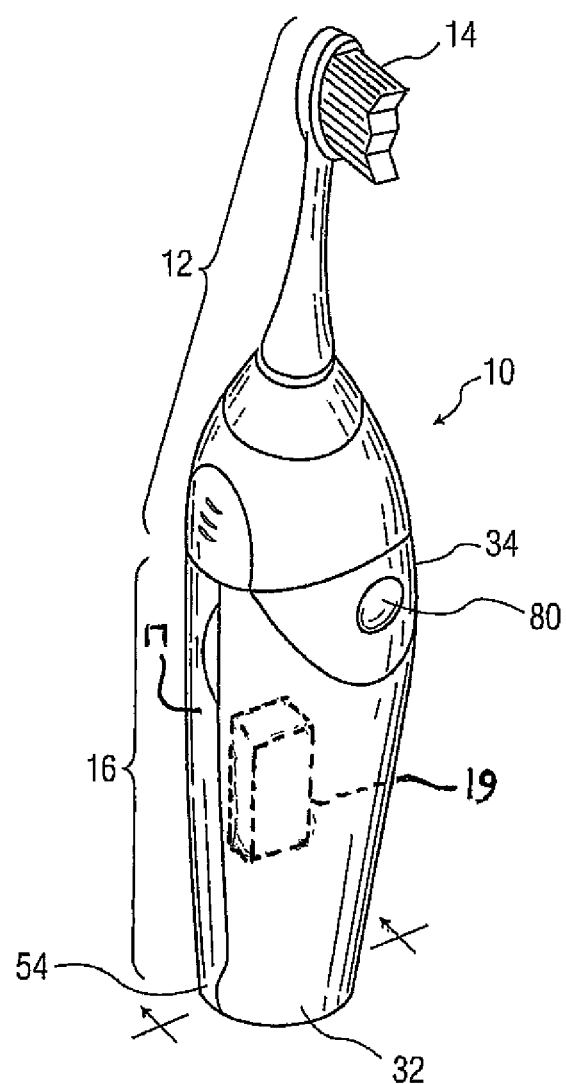
FIG. 1 is a schematic view of a fluid-dispensing toothbrush with a reservoir cover structure of the present embodiment, shown in a closed position.
Figure 2:
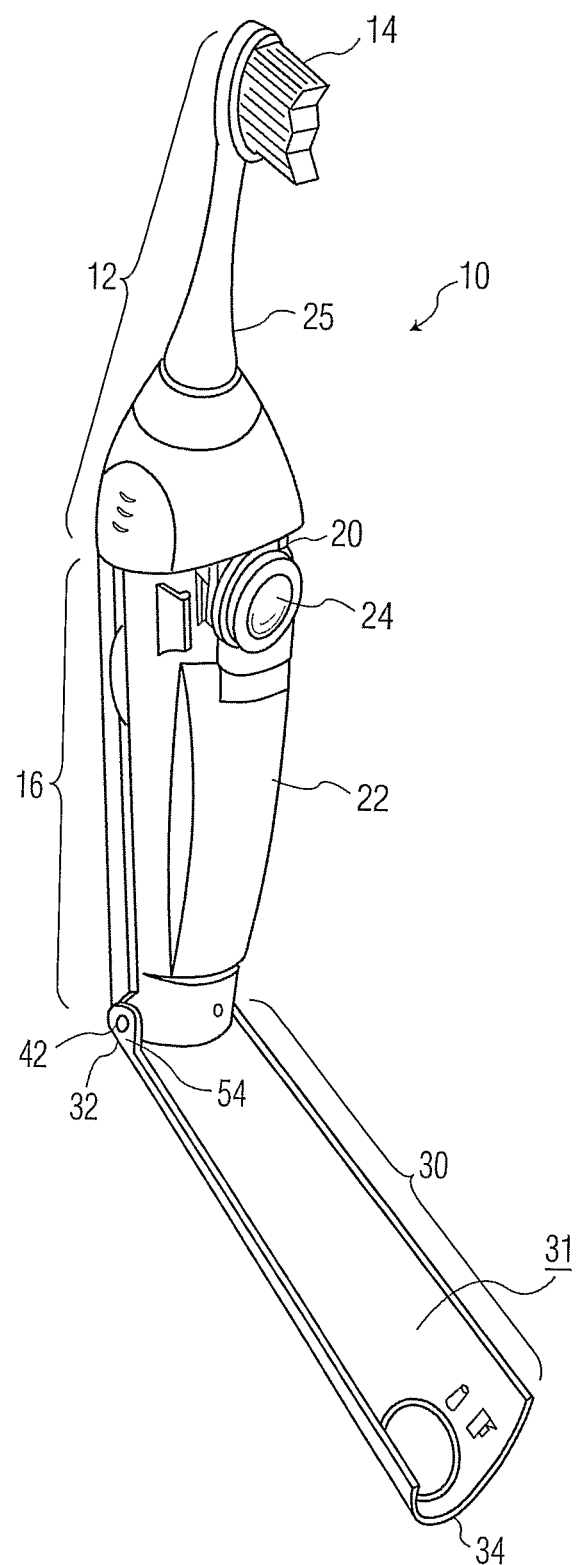
FIG. 2 is a schematic view similar to that of FIG. 1, with the reservoir cover shown in an open position.
Figure 3:
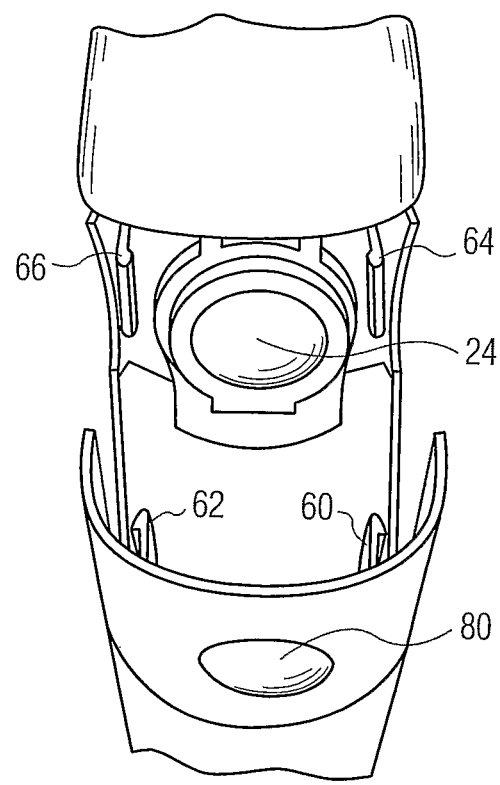
FIGS. 3 and 4 are partial perspective views showing the relationship of a user button on the cover relative to an operator button of the pump structure for the fluid, to which a fluid cartridge is connected.

Referring to FIGS. 1 and 2, a fluid-dispensing power toothbrush is shown generally at 10. Toothbrush 10 includes the head portion 12, which includes a conventional brushhead 14. Toothbrush 10 also includes a handle portion 16 having an exterior surface/housing 17 in which is located a drive system 19 for moving the brushhead 14 in a selected manner. In many such toothbrushes, head portion 12 is removable from handle portion 16. However, it should be understood that the power toothbrush 10 described here in general can take many different configurations and arrangements.

Further, fluid-dispensing toothbrush 10 includes a pump assembly 20 and a fluid-filled disposable reservoir (cartridge) 22 (FIG. 2). A suitable pump assembly is shown in U.S. Pat. No. 5,993,180, while a suitable reservoir is shown in U.S. patent application Ser. No. 60/482,914, the contents of both of which are incorporated herein by reference.

Pump assembly 20 includes an actuation button 24. Pressing inwardly on actuation button 24 activates the pump, resulting in delivery of fluid from reservoir 22 to the brushhead 14 through a connecting fluid line and a hollow brushhead stem 25. This structure is described in more detail in the co-pending patent application entitled "Structural Arrangement for a Fluid-Dispensing Power Toothbrush", owned by the assignee of the present invention, the contents of which are hereby incorporated by reference.

The cover in the embodiment shown and described herein is shown generally at 30. It extends from a lower end 32 of the handle 16 to an upper end 34 thereof, covering substantially the entire length of handle 16. Cover 30 is curved in cross-sectional configuration so that when it is in its closed position, it overlays a significant portion of handle 16, forming part of the exterior surface of the lower portion of the toothbrush, i.e. an extended diameter handle portion. In the embodiment shown, cover 30 is slightly narrower at the lower end than at the upper end thereof, following the shape of the handle. In the embodiment shown, cover 30 covers approximately 50 percent of the circumferential exterior surface of the toothbrush over the length of the cover. The cover is made from plastic in the embodiment shown, although it can be made from other materials. Typically, the cover is flexible to some extent, and can be transparent.

In the embodiment shown, the curved inner surface 31 of the cover is generally in the form of a half-oval, with the diameter of the oval gradually increasing in length from the lower or rear end of the cover where the cover is approximately a half-circle, to the upper end thereof. The gradual change from a half-circle configuration to a half-oval configuration, with an increasing diameter, results in a convenient gripping arrangement for the user. At the lower end of the cover, the diameter of the full circle is approximately 1¼ inches, while at the top end, the long axis of the oval is approximately 2¼ inches, and the short axis is approximately 1½ inches. This configuration results in a space between the cover and the exterior surface 23 of the handle.

The cover overlays reservoir 22, which extends along the exterior surface 23 of handle portion 16. Typically, reservoir 22 will be made from flexible material. The interior surface 31 of the cover is configured so that as the cover 30 is closed, the cover comes against reservoir 22, forming it to the curved configuration of the exterior surface of the handle. This is advantageous, since it helps to minimize the space necessary for the reservoir in the toothbrush.

Besides form-fitting the flexible reservoir 22 to the exterior surface 23 of handle 16 in the three-dimensional volume between the exterior surface of handle 16 and the interior surface of cover 30, closing the cover against the reservoir forces a small portion of the fluid in the reservoir into the pump, priming the pump. Accordingly, a first pressure on the actuation button 24 results in movement of fluid to the brushhead for dispensing.

The overall shape of cover 30 is also significant, in that its generally oval cross-section results in a good fit to the hand of the user and provides a natural anti-rotation characteristic/ feel for the user, as the toothbrush is used. The oval cross-section improves the grip of the appliance during brushing, without the necessity of using soft-touch material, which would increase the cost of the appliance.

Cover 30 is hingedly connected to the lower end of the handle by two opposing pins 42 and 44, which are coaxial, separated by approximately 180°. Pins 42 and 44 taper inwardly, in a direction toward each other, and engage mating tapered coaxial openings 46 and 48 on opposing surfaces of handle 16. The combination of the tapered pins 42 and 44 and the associated openings 46, 48 results in a reasonably secure retention of the cover, but also permits relatively convenient and easy removal of the cover from the handle without damage to the cover. In the embodiment shown, the pins are approximately 1/16-inch long, mating with similarly dimensioned openings in the handle.

Figure 6:
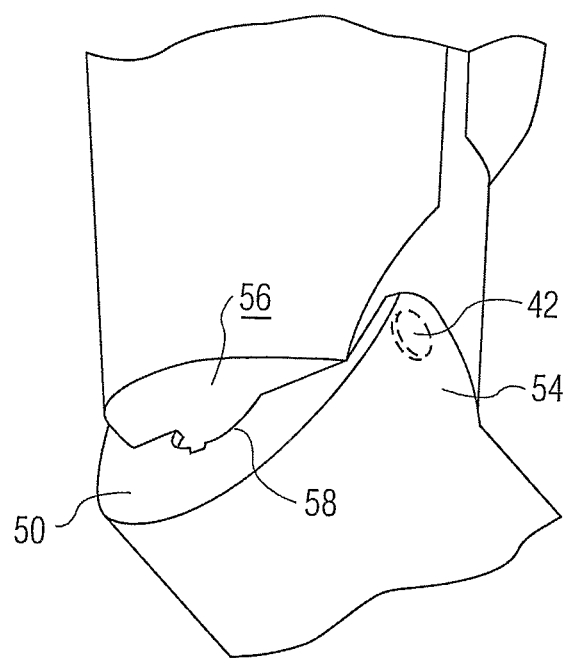
FIG. 6 is a perspective view showing the arrangement of the cover relative to the lower end of the handle when the cover is fully open.
Figure 7:
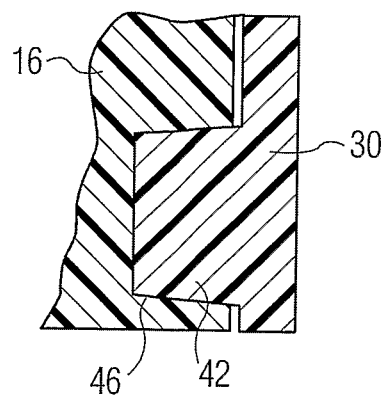
FIG. 7 is a cross-sectional view showing the pin structure joining the cover to the handle.
Figure 8:
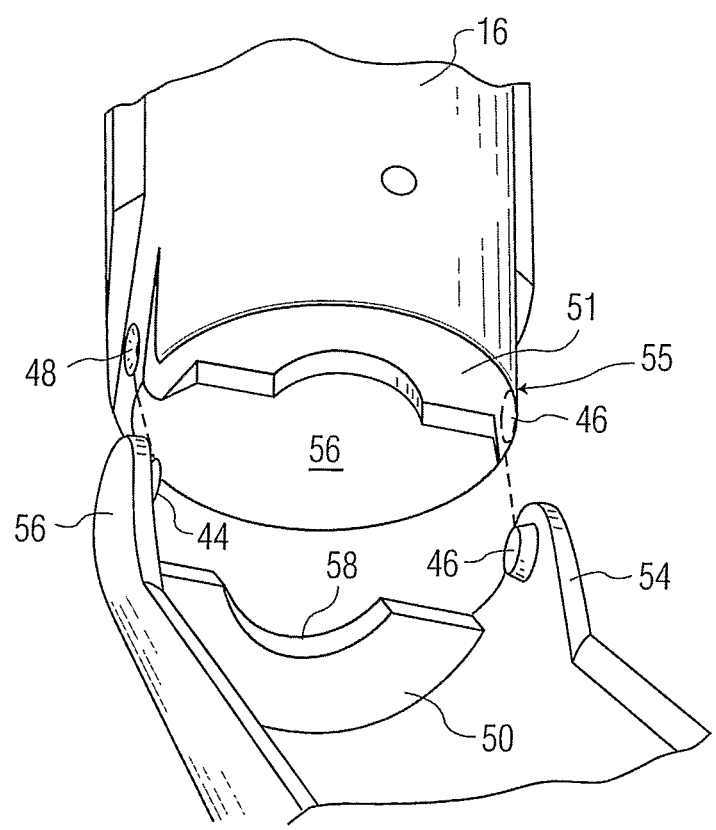
FIG. 8 is a perspective view showing the detailed arrangement of the cover relative to the lower end of the handle.

The lower end of cover 30 includes a bottom portion 50 which is normal to the remainder of the cover. In the embodiment shown, pins 42 and 44 extend inwardly from two ear portions 54 and 56 at the lower end of the longitudinal edges of the cover. The bottom portion 50 in the embodiment shown is half-annular in configuration, with the thickness of annular portion 50 being approximately 3/8 inch. The bottom portion 50 mates with a shallow (the thickness of the bottom portion 50) cutout portion 51 in the lower end 55 of the handle. When the cover 30 is in its open position, as shown in FIGS. 2 and 6 (FIG. 8 shows cover 30 extended away from handle 16), edge 58 of the bottom portion 50 of the cover abuts against a lower surface 56 of the handle, which acts as a stop against further rotation of the handle, at an angle of approximately 120° between the handle and the cover.

Further pressure downwardly on the handle results in the tapered pins 42, 44 coming out from the mating openings 46, 48, separating the cover from the handle. This arrangement provides a convenient removal capability of the cover from the handle, without risk of damage to the cover, and permits the cover to be readily replaced or cleaned when desired. The removed cover or a new one is readily snapped back into place, with the pins 42, 44 engaging the mating openings in the handle.

Hence, the pins and the end configuration of the cover prevents the cover from separating too easily, but permits ready removal and replacement of the cover when necessary or desired. Further, the stop provided by the same elements results in the cover being positionable at a convenient angle for replacement of the cartridge.

Figure 4:
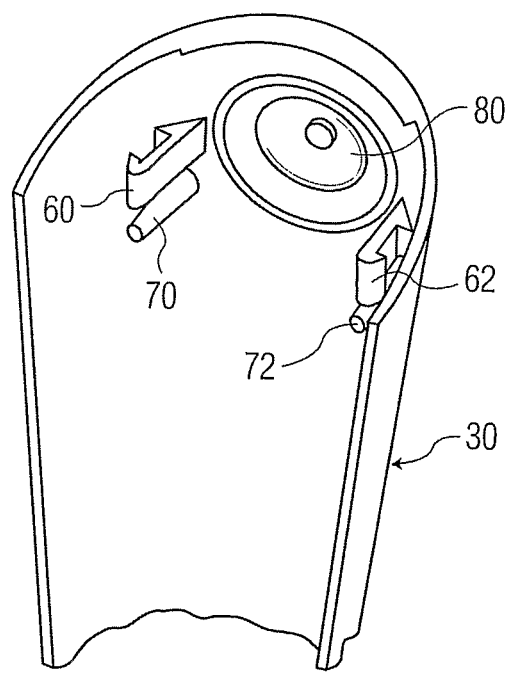

At the top of the cover, extending from the interior surface thereof are two latch elements 60 and 62 (FIG. 4). In the embodiment shown, latch elements 60 and 62 mate with corresponding receiving elements 64 and 66, which are configured to receive the latch elements and hold the cover in place in the closed position. The cover is moved from its closed position by grasping the cover along opposing longitudinal edges near the top end of the cover and pulling outwardly therefrom. Positioned below each latching element 60 and 62 are protrusions 70 and 72, which mate against corresponding surfaces of receiving elements 64 and 66, to provide a guiding function and a hard stop for the cover as it is moved into its closed position.

While the cover embodiment shown is hinged at the bottom and latched at the top, the reverse could be done, with the cover hinged at the top and latched at the bottom. Also, the cover could be hinged along one side and latched at the other side.

Figure 5:
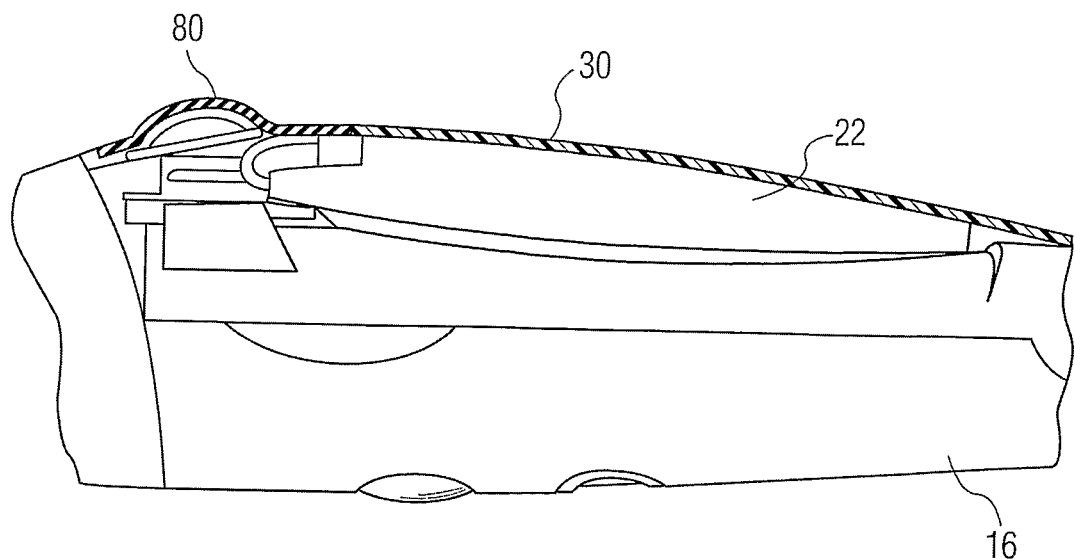
FIG. 5 is a cross-sectional view showing the relationship between the user's button for the pump on the cover and the pump actuation element, when the cover is in a closed position.

The cover 30 also includes an integral "soft-touch" button 80 which is positioned directly over and substantially adjacent to the actuation button for the pump when the cover 30 is in its closed position. Button 80 has a "dome" configuration, shown most clearly in FIG. 5. The soft-touch button 80 is made of elastomeric material which fits over an opening in the cover and in operation of the toothbrush is pressed inwardly by the user a short distance, contacting the actuation button. Further pressure on the button 80 results in actuation of the pump and delivery of fluid to the brushhead. When the button 80 is released, it rebounds to its original dome configuration. In the arrangement shown, button 80 is circular, approximately 5/8 inches in diameter, substantially identical to the actuation button of the pump. This arrangement has several advantages, including protection of the actuation button on the pump during use, as well as fast, convenient action for the user. Further, the control soft-touch button 80 hides the actuation button, such that the appearance of the actuation button is not important.

Alternatively, the cover 30 could have an opening in the vicinity of the button 80, approximately the same size as button 80. In this arrangement, button 80 could come up to the opening and the user would actuate button 80 directly to pump the fluid. In another arrangement, the toothbrush could be configured such that the actuation button is part of the head portion of the toothbrush with the cover otherwise remaining the same, overlaying the reservoir.

Accordingly, what has been disclosed is a cover for use in a fluid-dispensing toothbrush for covering a reservoir which extends along an outside surface of the handle. The cover provides a convenient exterior shape for the toothbrush, and is connected in such a way to provide a convenient access to the reservoir, while also being readily removable.

Although a preferred embodiment of the invention has been disclosed for purposes of illustration, it should be understood that various changes, modifications and substitutions can be incorporated in the embodiment without departing from the spirit of the invention which is defined by the claims which follow.

The invention claimed is:

1. A fluid dispensing power toothbrush, comprising:
 a head portion which includes a brushhead;
 a handle portion which includes a housing, defining an internal space in which is located a drive system for moving the brushhead;
 a fluid system which includes a single, undivided fluid reservoir having a length and sufficient fluid therein for multiple uses and a fluid pump separate from the fluid reservoir which moves fluid in successive user-initiated actions from the single fluid reservoir to the brushhead, by operation of an actuation member portion of the fluid pump, wherein the fluid reservoir and the fluid pump are positioned along an outer surface of the housing of the handle in operation of the toothbrush;
 a cover member configured to overlay and mate with a portion of the housing of the handle and to overlay the length of the fluid reservoir and at least the actuation member portion of the fluid pump, forming an exterior surface of a lower portion of the toothbrush when the cover member is in a closed position, wherein the cover member is configured relative to the outer surface of the housing to define a space therebetween to accommodate the fluid reservoir when the cover member is in a closed position, and wherein the fluid reservoir is accessible for removal when the cover member is in its open position; and a connector assembly for movably attaching the cover member to the housing to permit the cover member to move between said open and closed positions.

2. The cover member of claim 1, wherein the connector assembly is located near the bottom of the cover member and the handle, permitting pivoting movement of the cover member between open and closed positions relative to the handle.

3. The cover member of claim 2, wherein the cover member includes a latch member near the top end thereof and the handle includes a receiving member for the latch member, to secure the cover in its closed position.

4. The cover member of claim 2, wherein the connector assembly includes two opposing tapered pin elements which extend inwardly toward each other from an interior surface of the cover member, and further includes two mating tapered openings in the handle portion for rotatably receiving said pin elements.

5. The cover member of claim 4, wherein the pin elements are approximately 1/16-inch high.

6. The cover member of claim 1, wherein the cover member has a curved configuration which forms a part of the exterior surface of a lower portion of the toothbrush.

7. The cover member of claim 1, wherein the cover member has an interior surface which is configured and arranged such that when the cover member moves into its closed position, the cover member shapes the reservoir against an exterior surface of the handle portion, thereby minimizing the space required for the reservoir in the toothbrush.

8. The cover member of claim 7, wherein the interior surface of the cover member is configured to move a portion of fluid to the fluid pump when the cover member moves into its closed position, thereby priming the pump, following installation of a new reservoir in the toothbrush.

9. The cover member of claim 1, wherein the cover member has a lower end element configured such that, when the cover member is open, it acts as a stop against a lower end of the handle portion to stop further rotation of the cover member when the cover member reaches a selected angle relative to the handle portion.

10. The cover member of claim 9, wherein the angle is approximately 120°.

11. The cover member of claim 1, wherein the cover member includes a button member as part of its surface, overlaying an actuation button for the fluid pump, and wherein the cover member button is adapted and constructed such that it moves inwardly under pressure against a pump actuation element and rebounds to an original shape when pressure on the button is released.

12. The cover member of claim 1, wherein the cover member includes an opening in registry with an actuation member on the fluid pump, permitting a user to actuate the pump when the cover is in a closed position.

* * * * *